United States Patent [19]

Welstead, Jr. et al.

[11] 3,975,531
[45] Aug. 17, 1976

[54] 4-(5- AND 7-)BENZOYLINDOLIN-2-ONES AND PHARMACEUTICAL USES THEREOF

[75] Inventors: William John Welstead, Jr.; Henry Wayne Moran, both of Richmond, Va.

[73] Assignee: A. H. Robins Company, Incorporated, Richmond, Va.

[22] Filed: Jan. 29, 1975

[21] Appl. No.: 545,057

Related U.S. Application Data

[63] Continuation-in-part of Ser. No. 402,700, Oct. 2, 1973, abandoned, which is a continuation-in-part of Ser. No. 254,284, May 17, 1972, abandoned.

[52] U.S. Cl. .............................. 424/274; 260/325 R; 260/326.13 R; 260/470; 260/471 R; 260/516; 260/518 R
[51] Int. Cl.² ................. C07D 209/34; A61K 31/40
[58] Field of Search .................. 260/325 R; 424/274

[56] References Cited
UNITED STATES PATENTS
3,679,701   7/1972   Hester ...................... 260/326.11 R

*Primary Examiner*—Lewis Gotts
*Assistant Examiner*—S. P. Williams

[57] ABSTRACT

Novel 4-(5- and 7-)benzoylindolin-2-ones of the formula:

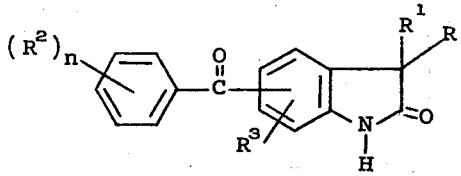

wherein R is hydrogen, lower-alkyl, or methylthio, $R^1$ is hydrogen or lower-alkyl, $R^2$ is lower-alkyl, lower-alkoxy, halogen, nitro or trifluoromethyl, $R^3$ is hydrogen, halogen or lower-alkoxy, and n is 0, 1 or 2, are prepared by (a) acylation of indolin-2-one to give 5-benzoylindoline-2-one, (b) cyclization of 2-acetamido-3-benzoylphenylacetic acid or ethyl 2-acetamido-3-benzoylphenylacetate to give 7-benzoyindoline-2-one, or (c) by reacting aminobenzophenones with alkyl α(methylthio)acetates to give alkyl 2-amino-3-(5- or 6-)benzoyl-α-(methylthio)phenylacetates which are cyclized and demethylthiolated to 4-(5- and 7-)benzoylindolin-2-ones. The novel compounds possess anti-inflammatory activity and are intermediates for the preparation of 2-amino-3-(5- or 6-) benzoylphenylacetic acids which posess anti-inflammatory properties.

31 Claims, No Drawings

4-(5- AND 7-)BENZOYLINDOLIN-2-ONES AND PHARMACEUTICAL USES THEREOF

The present invention is a continuation-in-part application of copending application Ser. No. 402,700 filed Oct. 2, 1973, now abandoned which is a continuation-in-part application of Ser. No. 254,284 filed May 17, 1972, now abandoned.

The present invention relates to novel indolin-2-ones and is more particularly concerned with 4-(5- and 7-) benzoylindolin-2-ones, compositions thereof, and the production and use of the same.

The novel compounds have the formula:

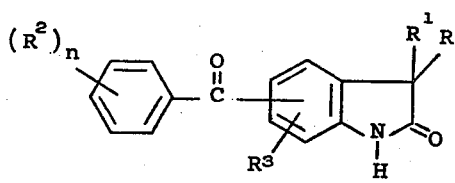

Formula I wherein;
R is hydrogen, lower-alkyl or methylthio,
$R^1$ is hydrogen or lower-alkyl,
$R^2$ is halogen, lower-alkyl, lower-alkoxy, nitro or trifluoromethyl,
$R^3$ is hydrogen, halogen or lower-alkoxy, and $n$ is 0, 1 or 2.

The compounds of the invention having the foregoing Formula I represent new chemical compounds which have the capacity to produce physiological action and are adapted more particularly for use as anti-inflammatory agents. The anti-inflammatory properties of the novel indolin-2-ones of Formula I were determined by the standard pharmacological procedures of Sancilio, L. F., J. Pharmacol. Exp. Ther. 168, 199–204 (1969).

In the procedure of Sancilio, edema, a sign of inflammation, can be seen as pleural fluid which effuses into the pleural cavity. Evans Blue-Carrageenan injected into the pleural cavity of mice produces edema and an increase in the volume of the pleural fluid. Compounds which possess anti-inflammatory activity possess the property of reducing the volume of pleural fluid produced by the intrapleural injection of Evans Blue-Carrageenan. When compounds are tested for anti-inflammatory activity according to the method of Sancilio, acetylsalicylic acid is tested at the same time as the control compound, the dose for a test compound and acetylsalicylic acid being 316 mg/kg orally.

The novel 4-(5- and 7-)benzolindolin-2-ones of the present invention are useful intermediates for the preparation of novel 2-amino-3-(5- and 6-)benzoylphenylacetic acids described in copending application Ser. No. 487,499, now abandoned.

It is, accordingly, an object of the present invention to provide novel compounds having anti-inflammatory properties. A further object is to provide methods for producing the novel compounds and methods for the utilization thereof. Additional objects will become apparent hereinafter and still others will be apparent to one skilled in the art.

In the definition of symbols in the formulas hereof and where they appear elsewhere throughout this specification, the terms have the following significance.

The term "lower-alkyl" as used herein includes straight and branched chain radicals of up to six carbons inclusive, preferably no more than four carbon atoms, and is exemplified by such groups as methyl, ethyl, propyl, isopropyl, butyl, sec. butyl, tertiary butyl, amyl, isoamyl, hexyl and the like. Lower-alkoxy has the formula -O-lower-alkyl.

When halogen is referred to herein, preferably but not necessarily a halogen of atomic weight not greater than eighty is employed.

METHOD OF PREPARATION

The preparation of the 4-(5- and 7-)benzoylindolin-2-ones may be accomplished by (a) mixing and reacting an indolin-2-one (II) with a benzoyl chloride (III) to give a 5-benzoylindolin-2-one (I), (b) a cyclization of an ethyl 2-acetamido-3-benzoylphenylacetate (IV) or a 2-acetamido-3-benzoylphenylacetic acid (IVa) to give a 7-benzoylindolin-2-one (I), or (c) by reacting aminobenzophenones with alkyl α-(methylthio)acetates to give alkyl 2-amino-3-(5- or 6-)benzoyl-α-(methylthio)-phenylacetates which are cyclized and demethylthiolated to 4-(5- or 7-)benzoylindolin-2-ones. The reaction sequences are:

(a) 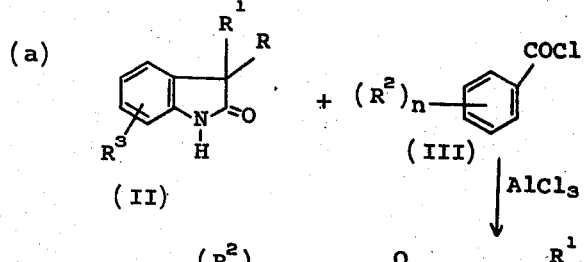

(b) 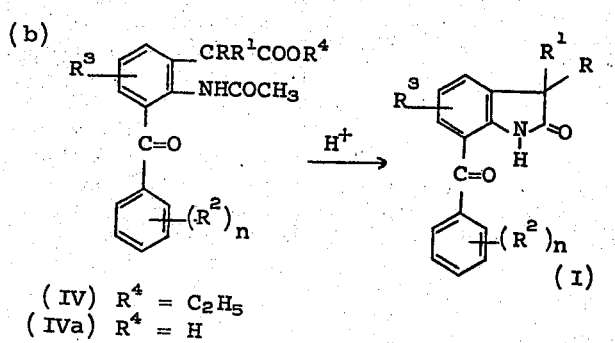

(IV) $R^4 = C_2H_5$
(IVa) $R^4 = H$

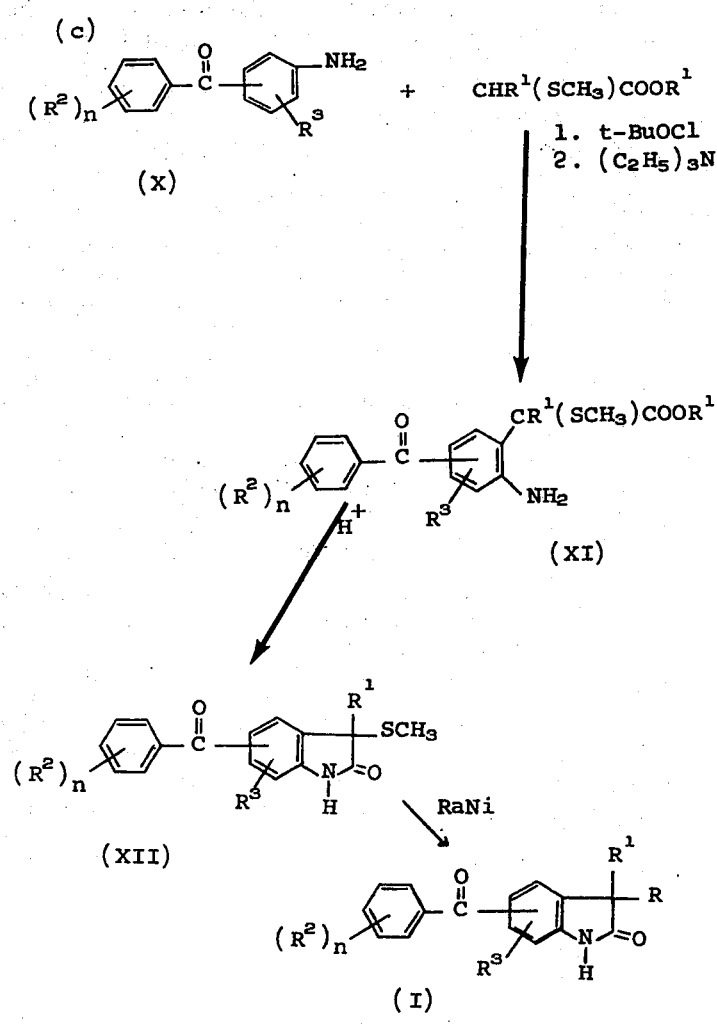

In process (a) acylation of an indolin-2-one (II) to give a 5-benzoylindolin-2-one (I) is carried out under reaction conditions generally employed in a Friedel-Craft reaction, the limitation being that $R^2$ and $R^3$ are non-reactive under the reaction conditions employed.

In process (b) the cyclization of ethyl 2-acetamido-3-benzoylphenylacetate (IV) and/or 2-acetamido-3-benzoylphenylacetic acid (IVa) to 7-benzoylindolin-2-one (I) is carried out in dilute mineral acid solution.

In process (c) a solution of a selected aminobenzophenone (X) in a halogenated organic solvent, e.g., methylene chloride, is treated at −50° to −78°C. with t-butylhypochlorite and then with a lower alkyl α-(methylthio)acetate as, for example, ethyl α-(methylthio)acetate to give an ethyl 2-amino-3-(5- or 7-) benzoyl-α-(methylthio)acetate (XI) which can be isolated or can be converted in situ by the addition of a dilute mineral acid such as dilute hydrochloric acid to a 3-methylthio-4-(5- or 7-) benzolindolin-2-one (XII). The 3-methylthio group is removed by stirring a dry tetrahydrofuran solution of the 3-methylthio compound (XII) with Raney-Ni under an inert gas to give a benzoylindolin-2-one of Formula I.

The indolin-2-ones (II) are commercially available or can be readily prepared by methods known to the art such as are disclosed by Wenkert et al., J. Am. Chem. Soc. 81, 3763–3768 (1959).

The ethyl 2-acetamido-3-benzoylphenylacetate (IV) and 2-acetamido-3-benzoylphenylacetic acids (IVa) are prepared by the following sequence of reactions starting with 1-aminoindolin-2-ones (V). The latter comopunds are prepared by the method of Baumgarten et al., J. Am. Chem. Soc. 82, 3977–3982 (1960).

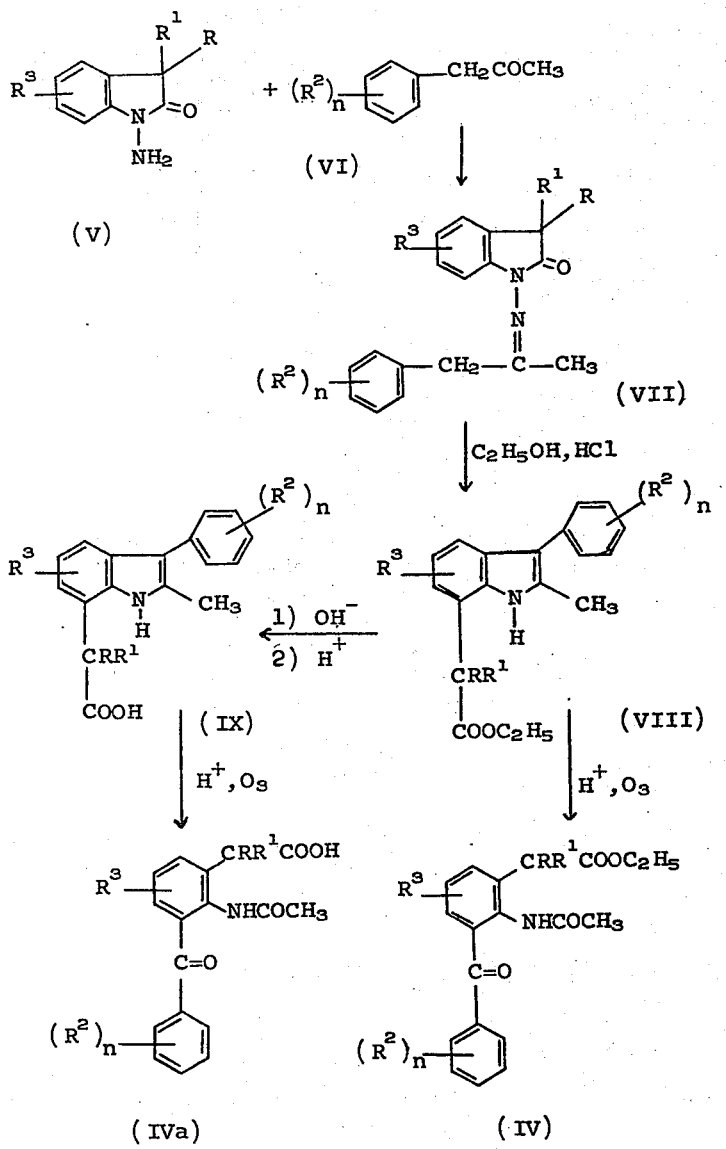

A 1-aminoindolin-2-one (V) is reacted with a phenylacetone (VI) is ethanol containing a catalytic amount of acetic acid to give a 1-(α-methylphenethylindenimino)indolin-2-one (VII). The latter compound is heated in a lower alkanol, preferably ethanol, which is saturated with hydrogen chloride to give an ethyl α-(2-methyl-3-phenylindol-7-yl)acetate (VIII) which is treated with ozone in acetic acid to give an ethyl 2-acetamido-3-benzoylphenylacetate. The alternate starting material, a 2-acetamido-3-benzoylphenylacetic acid (IVa), is obtained by basic hydrolysis of an ester (VIII) to an acid (IX) which is treated with ozone in acetic acid to give a 2-acetamido-3-benzoylphenylacetic acid (IVa).

PREPARATION 1

1-(α-Methylphenethylidenimino)indolin-2-one.

A mixture of 10 g. (0.07 mole) of 1-aminoindolin-2-one and 9.05 g. (0.07 mole) of phenylacetone in 65 ml. of absolute ethanol was heated until all the 1-aminoindolin-2-one dissolved. The solution was treated with 0.5 ml. of acetic acid and heated on a steam bath an additional 15 minutes. After cooling, the product was filtered off and the filtrate was treated with water. The additional product which precipitated from the filtrate was combined with the original material and recrystalized from absolute alcohol; yield 16 g. (90%); m.p. 102°–104°C.

Analysis: Calculated for $C_{17}H_{16}N_2O$: C, 77.25; H, 6.10; N, 10.60. Found: C, 77.26; H, 6.16; N, 10.58.

PREPARATION 2

Ethyl α-(2-methyl-3-phenylindol-7-yl)acetate

A solution of ethanolic hydrogen chloride was prepared by bubbling dry hydrogen chloride into 100 ml. of absolute ethanol until the solution began to boil. At this point 10 g. (0.04 mole) of 1-(α-methylphenethylidenimino)indolin-2-one was added and the mixture was stirred for 30 minutes. Additional hydrogen chloride was bubbled into the hot mixture until thin layer chromatography showed no starting material remained. The reaction mixture was allowed to cool and the solid which separated from the cooled reaction mixture was filtered off. The solid was 1-aminoindolin-2-one. The filtrate was concentrated and the residual brown oil was shown by nuclear magnetic resonance to be a mixture of phenylacetone and product. The mixture was distilled at 165°–175°C. (0.5 mm.); the oil distillate solidified upon cooling. The solid was recrystallized from ligroin to give ethyl α-(2-methyl-3-phenylindol-7-yl)acetate which melted at 108°–109°C. and weighed 2.2 g. (21%).

Analysis: Calculated for $C_{19}H_{19}NO_2$: C, 77.79; n, 6.53; N, 4.77. Found: C, 77.60; H, 6.54; N, 4.77.

PREPARATION 3

α-(2-Methyl-3-phenylindol-7-yl)acetic Acid.

To a solution of 8 g. of potassium hydroxide in 100 ml. of water was added 6 g. (0.2 mole) of ethyl α-(2-methyl-3-phenylindol-7-yl-acetate. The mixture was refluxed for two hours. The cooled reaction mixture was filtered and the filtrate diluted with an equal volume of water. Acidification of the basic solution with 3N hydrochloric acid gave α-(2-methyl-3-phenylindol-7-yl)acetic acid which was recrystallized from benzene; yield 3.7 g. (67%); m.p. 165°C. (dec.).

Analysis: Calculated for $C_{17}H_{15}NO_2$: C, 76.96; H, 5.70; N, 5.28. Found: C, 77.90; H, 5.70; N, 5.22.

PREPARATION 4

Ethyl 2-acetamido-3-benzoylphenylacetate.

A solution of 5 g. (0.017 mole) of ethyl α-(2-methyl-3-phenylindol-7-yl)acetate and 75 ml. of acetic acid was treated with ozone for 25 minutes. After ozonation, the acetic acid solution was diluted with water and extracted with ether. The ether extracts were washed with water, 5% sodium carbonate, dried (magnesium sulfate) and concentrated. Recrystallization from isopropanol gave 2.6 g. (47%) of product which melted at 133°–134°C.

Analysis: Calculated for $C_{19}H_{19}NO_4$: C, 70.14; N, 5.89; N, 4.30. Found: C, 69.95; H, 5.99; N, 4.12.

PREPARATION 5

2-Acetamido-3-benzoylphenylacetic Acid.

A solution of 2 g. of α-(2-methyl-3-phenylindol-7-yl)acetic acid in 60 ml. of acetic acid was treated with ozone for 15 minutes. The reaction mixture was treated with 10 ml. of water and allowed to evaporate overnight. The residue (1.7 g.) was recrystallized from isopropanol; yield 1.6 g. (71%); m.p. 188°–190°C. Analysis: Calculated for $C_{17}H_{15}NO_4$: C, 68.68; H, 5.08; N, 4.71. Found: C, 68.33; H, 5.11; N, 4.58.

PREPARATION 6

Other 1-(α-methylphenethylidenimino)indolin-2-ones. — 1(α-methyl-p-chlorophenethylidenimino)indolin-2-one, 1-(α-methyl-o-fluorophenethylidenimino)indolin-2-one and 1-(α-methyl-m-trifluoromethylphenethylideimino)indolin-2-one are prepared in the same manner of Preparation 1 from 1-aminoindolin-2-one and the corresponding substituted phenylacetone.

PREPARATION 7

Other ethyl α-(2-methyl-3-phenylindol-7-yl)acetates. — ethyl α [2-methyl-3-(p-chlorophenyl)indol-7-yl]acetate, ethyl α-[2-methyl-3-(o-fluorophenyl)indol-7-yl]acetate and ethyl α-[2-methyl-3-(m-trifluoromethylphenyl)indol-7-yl]acetate are prepared in the same manner of Preparation 2 from the corresponding 1-(α-methylphenethylidenimino)indolin-2-one.

PREPARATION 8

Other α-(2-methyl-3-phenylindol-7-yl)acetic acids. — α-[2-methyl-3-(p-chlorophenyl)indol-7-yl]acetic acid, α-[2-methyl-3-(o-fluorophenyl)indol-7-yl]acetic acid and α-[2-methyl-3-(m-trifluoromethylphenyl)indol-7-yl]acetic acid are prepared in the same manner of Preparation 3 from the corresponding ethyl α-(2-methyl-3-phenyl-indol-7yl)acetate.

PREPARATION 9

Other ethyl 2-acetamido-3-benezolylacetates. — ethyl 2-acetamido-3-(p-chlorobenzoyl)phenylacetate, ethyl 2-acetamido-3-(o-fluorobenzoyl)phenylacetate and ethyl 2-acetamido-3-(m-trifluoromethylbenzoyl)-phenylacetate are prepared in the same manner of Preparation 4 by ozonation of the corresponding ethyl α-(2-methyl-3-phenylindol-7-yl)acetates.

PREPARATION 10

Other 2-acetamido-3-benzoylphenylacetic acids. — 2-acetamido-3-(p-chlorobenzoyl)phenylacetic acid, 2-acetamido-3-(o-flurorobenzoyl)phenylacetic acid and 2-acetamido-3-(m-trifluoromethylbenzoyl)-phenylacetic acid are prepared in the same manner of Preparation 5 by ozonation of the corresponding α-(2-methyl-3-phenylindol-7-yl)acetic acids.

EXAMPLE 1

7-Benzoylindolin-2-one.

Method A

A mixture of 2.5 g. (0.0077 mole) of ethyl 2-acetamido-3-benzoylphenylacetate in 50 ml. of 3N hydrochloric acid was refluxed for one hour. The reaction mixture was filtered and the filtrate was poured into a mixture of ice and water. The precipitate was collected and recrystallized from acetone; yield 1 g. (55%); m.p. 154°C.

Analysis: Calculated for $C_{15}H_{11}NO_2$: C, 75.94; H, 4.67; N, 5.90. Found: C, 75.84; H, 4.76; N, 5.78.

Method B

A solution of 1.3 g. (0.0044 mole) of 2-acetamido-3-benzoylphenylacetic acid in 15 ml. of 3N hydrochloric acid and 15 ml. of acetic acid was refluxed for three hours. The cooled solution was poured into ice water and the 7-benzoylindolin-2-one which precipitated was collected and dried.

EXAMPLE 2

5-Benzoylindolin-2-one.

A stirred slurry of 66 g. (0.5 mole) of aluminum chloride and 42.5 g. (0.3 mole) of benzoyl chloride was heated to 150°C. and then 133 g. (0.1 mole) of indolin-2-one was slowly added at a rate so that the temperature of the stirred reaction mixture was maintained at 180°–185°C. After addition the reaction mixture was stirred for five minutes at 185°C., cooled and poured into ice water. The 5-benzoylindolin-2-one which precipitated was collected and recrystallized from methanol; it melted at 204°–205°C. The yield was 17.5 g. (73%).

Analysis: Calculated for $C_{15}H_{11}N_1O_2$: C, 75.94; H, 4.67; N, 5.90. Found: C, 75.76; H, 4.69; N, 5.82.

EXAMPLE 3

Other 7-benzoylindolin-2-ones.- 7-(p-chlorobenzoyl)indolin-2-one, 7-(o-fluorobenzoyl)indolin-2-one and 7-(m-trifluoromethylbenzoyl)indolin-2-one are prepared in the same manner of Example 1 by cyclization of the corresponding ethyl 2-acetamido-3-benzoylphenylacetate or 2-acetamido-3-benzoylphenylacetic acid.

EXAMPLE 4

Other 5-benzoylindolin-2ones.- 5-(p-chlorobenzoyl)indolin-2-one, 5-(o-fluorobenzoyl)indolin-2-one, 5-(p-methoxybenzoyl) indolin-2-one and 5-(m-trifluoromethylbenzoyl)indolin-2-one are prepared in the manner of Example 2 from indolin-2-one and the corresponding substituted benzoyl chloride.

EXAMPLE 5

7-Benzoyl-5-chloroindolin-2-one.

A mixture of 162.5 g. (1.08 mole) of benzoyl chloride and 260 g. of aluminum chloride (1.80 mole) heated to 200°C. with stirring was treated with 65 g. (0.360 mole) of recrystallized 5-chloroindolin-2-one. This mixture was stirred 15 min. and poured over ice. The resulting precipitate was triturated with boiling water and then chloroform. The chloroform solution was washed with 5% sodium bicarbonate, water, dried over sodium sulfate, and stripped to yield approximately 55 g. of a glossy solid. This material was then triturated with hot methanol and the methanol evaporated under vacuum to yield approximately 20 g. of a solid yellow material. Extraction of a benzene solution of this material with conc. hydrochloric acid removed unreacted 5-chloroindolin-2-one and the benzene solution after washing with water and drying yielded on evaporation 3 g. of a blue-gray material. Trituration of this material with room temperature methanol gave a residue which on recrystallization from methanol yielded 2.5 g. of a tan solid identified as product, m.p. 186°–187°C.

Analysis: Calc'd for $C_{15}H_{10}ClNO_2$: C, 66.31; H, 3.71; N, 5.16. Found: c, 66.27; H, 3.83; N, 5.07.

EXAMPLE 6

7-Benzoyl-5-methoxyindolin-2-one.

7-Benzoyl-5-methoxyindolin-2-one is prepared by cyclization of the precursor 2-acetamido-3-benzoyl-5-methoxyphenylacetic acid or the lower alkyl ester thereof according to process c. The starting material is 1-amino-5-methoxyindolin-2-one which can be prepared according to the method of Baumgarten et al. The 7-benzoyl-5-methoxyindolin-2-one is a yellow powder which melts at 154°C.

Analysis: Calc'd for $C_{16}H_{13}NO_3$: C, 71.90; H, 4.90; N, 5.24. Found: C, 71.72; H, 5.15; N, 5.13.

EXAMPLE 7

4-Benzoyl-3-methylthioindolin-2-one.

A solution of 30.6. (0.152 mole) of 3-aminobenzophenone in 160 ml. of methylene chloride was cooled to −78°C. in a dry ice/acetone bath and treated dropwise under a nitrogen atmosphere with a solution of 16.5 g. (0.152 mole) of t-butylhypochlorite in 60 ml. of methylene chloride. After stirring for 1 hr. after addition was complete, thin layer chromatography showed no starting material. A solution of 20.2 g. (0.152 mole) of ethyl α-(methylthio)acetate in 60 ml. of methylene chloride was added dropwise and stirring continued at −78°C. for 2.5 hr. A solution of 15.4 g. (0.152 mole) of triethylamine in 60 ml. of methylene chloride was added dropwise at −78°C. and the reaction mixture allowed to warm to room temperature while stirring for 16 hr. (overnight). The dark brown solution was treated with 100 ml. of 3N hydrochloric acid and stirred for 3 hrs. at room temperature. Precipitation of a tan solid began after 15–30 minutes. Filtration gave 18.5 g. of solid, m.p. 224°–228°C. (dec.). The layers of the filtrate were separated, the organic phase dried over magnesium sulfate, evaporated under reduced pressure, and the residue triturated in isopropyl ether (25 g.). The gummy solid was triturated in cold methanol to give 8.3 g. of product, m.p. 222°–225°C. (dec.). The total yield was 26.8 g. (62%). A 7.0 g. sample recrystallized from methanol weighed 5.6 g. and melted at 235°–237°C. (dec.).

Analysis: Calc'd for $C_{16}H_{13}NO_2S$: C, 67.823; H; 4.625; N, 4.943. Found: C, 67.86; H, 4.71; N, 4.85.

EXAMPLE 8

7-(4-Chlorobenzoyl)-3-methylthioindolin-2-one.

A solution of 23.1 g. (0.1 mole) of 2-amino-4'-chlorobenzophenone in 400 ml. of methylene chloride was cooled to −65°C. and treated dropwise with 12.4 g. (0.1 mole) of t-butyl hypochlorite. After 15 min., 13.4 g. of ethyl α-(methylthio)acetate (0.1 mole) was added dropwise maintaining −65°C. temperature. After 1½ hr. 10.1 g. of triethylamine (0.1 mole) was added and the reaction mixture allowed to come to room temperature. The solution was then washed with water and stripped. The residue was taken into methanol and brought to reflux at which time 1N hydrochloric acid was added and the resulting mixture refluxed overnight. The mixture was cooled, resulting precipitate filtered off and recrystallized from toluene, giving 10 g. of a cream colored solid. The product (33% yield) melted at 186°–188°C.

Analysis: Calc'd for $C_{16}H_{12}ClNO_2S$: C, 60.47; H, 3.81; N, 4.41. Found: C, 60.29; H, 3.76; N, 4.43.

EXAMPLE 9

7-Benzoyl-3-methyl-3-methylthioindolin-2-one.

A stirred solution of 3.94 g. (0.02 mole) of 2-aminobenzophenone in methylene chloride at −65°C. was treated with 2.16 g. (0.02 mole) of t-butylhypochlorite. After 15 min. 2.96 g. ethyl α-(methylthio)propionate was added dropwise and stirring continued for 1 hr. At the end of this time 2.02 g. of triethylamine (0.02 mole) was added dropwise and the reaction solution was allowed to warm to room temperature. This was followed by treatment with 1N hydrochloric acid and stirred for 15 min. The methylene chloride solution was then separated and stripped under vacuum. The yellow oil residue was triturated with isopropyl ether and 3 g. of a yellow solid was filtered off (51%). Recrystallization from absolute ethanol gave a cream color solid, m.p. 135°–137°C.

Analysis: Calc'd for $C_{17}H_{15}NO_2S$: C, 68.66; H, 5.08; N, 4.71. Found: C, 68.54; H, 5.08; N, 4.63.

EXAMPLE 10

7-Benzoyl-3-methylthioindolin-2-one.

A solution of 300 g. (1.52 mole) of 2-aminobenzophenone in 4 liters of methylene chloride was chilled to −40°C. and then treated with 204 g. (1.52 mole) of the ethyl α-(methylthio)acetate dissolved in 5 liters of methylene chloride. The reaction mixture was then cooled to −65°C. and treated dropwise with 500 ml. of a methylene chloride solution containing 164 g. (1.52 mole) of t-butylhypochlorite. After addition was complete, stirring was continued for 2 hr. at −70°C. The solution was then treated with 182 g. (1.8 mole) of triethylamine and allowed to come to room temperature overnight. The methylene chloride solution was washed twice with 3 liters of ice water followed by drying over sodium sulfate and concentrating the dried solution to a yellow oil under reduced pressure. The oil was taken into 1.5 liters of methanol treated with 1 liter of 1N hydrochloric acid and refluxed for 2 hrs. After cooling in an ice bath 343 g. (79.9%) of crude product was recovered after filtering and drying. Two recrystallizations from toluene gave creamy white flakes; m.p. 130°C.

Analysis: Calc'd for $C_{16}H_{13}NO_2S$: C, 67.82; H, 4.62; N, 4.97. Found: C, 68.06; H, 4.68; N, 4.87.

EXAMPLE 11

4-Benzoylindolin-2-one.

A stirred suspension of 7.0 g. (0.0248 mole) of 4-benzoyl-3-methylthioindolin-2-one in 400 ml. of tetrahydrofuran was treated portionwise under a nitrogen atmosphere with 35.0 g. of Raney nickel over a 2.5 hr. period. The reaction mixture was stirred for 1.5 hr. after addition was complete and the catalyst removed by filtration. The filter cake was washed well with tetrahydrofuran and methylene chloride and the filtrate evaporated under reduced pressure. The residue (5.6 g.) was recrystallized from methanol and gave 4.45 g. (76%) of product m.p. 210°–212°C.

Analysis: Calc'd for $C_{15}H_{11}NO_2$: C, 75.937; H, 4.673; N, 5.904. Found: C, 75.85; H, 4.59; N, 5.92.

EXAMPLE 12

7-(4-Chlorobenzoyl)indolin-2-one.

A stirred solution of 9 g. (0.028 mole) of 7-(4-chlorobenzoyl)-3-methylthioindolin-2-one in 180 ml. of tetrahydrofuran was treated over a two-hour period with 45 g. of a commercial Raney nickel water suspension. After the addition was complete the mixture was filtered. A drop of concentrated hydrochloric acid was added to the filtrate which removed some color and the resulting solution was then stripped under water pump vacuum to yield a cream color material. Recrystallization from toluene gave pink needles, (93% yield); the material sintered at 177°C. and melted at 186°C.

Analysis: Calc'd for $C_{15}H_{10}ClNO_2$: C, 66.31; H, 3.71; N, 5.16. Found: C, 65,97; H, 3.56; N, 5.11.

EXAMPLE 13

7-Benzoyl-3-methylindolin-2-one.

A stirred solution of 8 g. (0.027 mole) of 7-benzoyl-3-methyl-3-methylthioindolin-2-one in 80 ml. of tetrahydrofuran was treated under $N_2$ with 40 g. of a commercial Raney nickel-water mixture over a 2 hr. period. At the end of this period the mixture was filtered and the residue washed thoroughly with tetrahydrofuran. One drop of concentrated hydrochloric acid was added to the filtrate and the dark orange solution turned pale yellow. The solution was stripped under vacuum to a yellow oil which crystallized on seeding. The material was recrystallized from toluene petroleum ether to give a white crystalline material. The solid (6.0 g., 89% yield) melted at 125°–127°C.

Analysis: Calc'd for $C_{16}H_{13}NO_2$: C, 76.43; H, 5.22; N, 5.57. Found: C, 76.38; H, 5.22; N, 5.52.

FORMULATION AND ADMINISTRATION

Effective quantities of the pharmacologically active compounds may be administered to a living animal body orally as in capsules and tablets. Fifty to one hundred milligrams appears optimum per unit dose, while usual broader ranges appear to be one to one hundred milligrams per unit dose. Several unit doses may be administered at the same time. The active agents of the invention can be combined with other pharmacologically active agents, or with buffers, antacids or the like. In forming the novel compositions of this invention, the active ingredient is incorporated in a suitable carrier, illustratively, a pharmaceutical carrier. Suitable pharmaceutical carriers which are useful in formulating the compositions of this invention include starch, gelatin, glucose, magnesium carbonate, lactose, malt and the like. Liquid compositions are also within the purview of this invention and suitable liquid pharmaceutical carriers include ethyl alcohol, propylene glycol, glycerin, glucose syrup and the like.

The following examples of compositions formed in accordance with this invention.

1. Capsule

Capsules of 50 mg. and 100 mg. of active ingredient per capsule are prepared.

| Typical Blend for Encapsulation | Per Capsule, mg. |
| --- | --- |
| Active ingredient | 50.0 |
| Lactose | 251.7 |
| Starch | 129.0 |
| Magnesium stearate | 4.3 |
| Total | 435.0 |

Additional capsule formulations preferably contain a higher dosage of active ingredient and are as follows:

| Ingredients | 100 mg. per Capsule |
| --- | --- |
| Active ingredient | 100.0 |
| Lactose | 231.5 |
| Starch | 99.2 |
| Magnesium stearate | 4.3 |
| Total | 435.0 |

In each case, uniformly blend the selected active ingredient with lactose, starch, and magnesium stearate and encapsulate the blend.

2. Tablets

A typical formulation for a tablet containing 50.0 mg. of active ingredient per tablet follows. The formulation may be used for other strengths of active ingredient by adjustment of weight of dicalcium phosphate.

|   |   | Per Tablet, mg. |
|---|---|---|
| 1. | Active ingredient | 50.0 |
| 2. | Milo starch | 20.0 |
| 3. | Corn starch (paste) | 38.0 |
| 4. | Lactose | 90.0 |
| 5. | Calcium stearate | 2.0 |
|   | Total | 200.0 mg. |

Uniformly blend the active ingredient, lactose, milo starch and the corn starch. This blend is granulated using water as a granulating medium. The wet granules are passed through an eight mesh screen and dried at 140° to 160°F. overnight. The dried granules are passed through a number ten mesh screen and blended with the proper amount of calcium stearate and this blend is then converted into tablets on a suitable tablet press.

Various modifications and equivalents will be apparent to one skilled in the art and may be made in the compounds, compositions, methods, and procedures of the present invention without departing from the spirit and scope thereof, and it is therefore to be understood that the invention is to be limited only by the scope of the appended claims.

What is claimed is:

1. A 4-(5- and 7-)benzoylindolin-2-one of the formula:

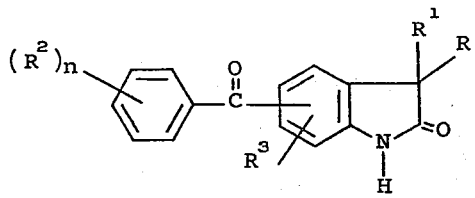

wherein;
  R is selected from the group consisting of hydrogen, lower-alkyl or methylthio,
  $R^1$ is selected from the group consisting of hydrogen or lower-alkyl,
  $R^2$ is selected from the group consisting of lower-alkyl, lower-alkoxy, halogen, nitro or trifluoromethyl,
  $R^3$ is selected from the group consisting of hydrogen, halogen or lower alkoxy, and $n$ is 0, 1 or 2.

2. The compound of claim 1 which is 5-benzoylindolin-2-one.

3. The compound of claim 1 which is 7-benzoylindolin-2-one.

4. The compound of claim 1 which is 4-benzoylindolin-2-one.

5. The compound of claim 1 which is 3-methyl-7-benzoylindolin-2-one.

6. The compound of claim 1 which is 3-(n-butyl)-5-benzoylindolin-2-one.

7. The compound of claim 1 which is 7-benzoyl-5-chloroindolin-2-one.

8. The compound of claim 1 which is 7-benzoyl-5-methoxyindolin-2-one.

9. The compound of claim 1 which is 7-(4-chlorobenzoyl)indolin-2-one.

10. A 4-(5- and 7-)benzoyl-3-methylthioindolin-2-one of the formula:

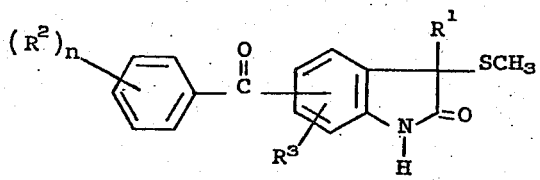

wherein;
  $R^1$ is selected from the group consisting of hydrogen or lower-alkyl,
  $R^2$ is selected from the group consisting of lower-alkyl lower-alkoxy, halogen, nitro or trifluoromethyl,
  $R^3$ is selected from the group consisting of hydrogen, halogen, or lower alkoxy, and $n$ is 0, 1 or 2.

11. The compound of claim 10 which is 4-benzoyl-3-methylthioindolin-2-one.

12. The compound of claim 10 which is 7-(4-chlorobenzoyl)-3-methylthioindolin-2-one.

13. The compound of claim 10 which is 7-benzoyl-3-methyl-3-methylthioindolin-2-one.

14. The compound of claim 10 which is 7-benzoyl-3-methylthioindolin-2-one.

15. A method of treating inflammation which comprises administering to an animal in need thereof an effective amount of a compound selected from the group consisting of 4-(5- and 7-)benzoylindolin-2-one of the formula:

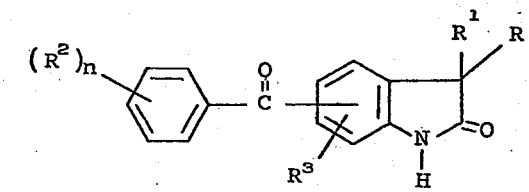

wherein:
  R is selected from the group consisting of hydrogen, lower-alkyl or methylthio,
  $R^1$ is selected from the group consisting of hydrogen or lower alkyl,
  $R^2$ is selected from the group consisting of lower-alkyl, lower-alkoxy, halogen, nitro or trifluoromethyl,
  $R^3$ is selected from the group consisting of hydrogen, halogen or lower alkoxy, and $n$ is 0, 1 or 2.

16. A method according to claim 15 wherein the active ingredient is administered together with a pharmaceutically acceptable carrier therefor and in an amount of about one to 100 milligrams.

17. The method of claim 16 wherein the active compound is 5-benzoylindolin-2-one.

18. The method of claim 16 wherein the active compound is 7-benzoylindolin-2-one.

19. The method of claim 16 wherein the active compound is 3-methyl-5-benzoylindolin-2-one.

20. The method of claim 16 wherein the active compound is 3-(n-butyl)-5-benzoylindolin-2-one.

21. The method of claim 16 wherein the active compound is 7-benzoyl-5-chloroindolin-2-one.

22. The method of claim 16 wherein the active compound is 7-benzoyl-5-methoxyindolin-2-one.

23. The method of claim 16 wherein the active compound is 7-(4-chlorobenzoyl)indolin-2-one.

24. A pharmaceutical composition, useful for its anti-inflammatory effect, comprising (a) an effective amount of about one to 100 milligrams of a 4-(5- and 7-)benzoylindolin-2-one of the formula:

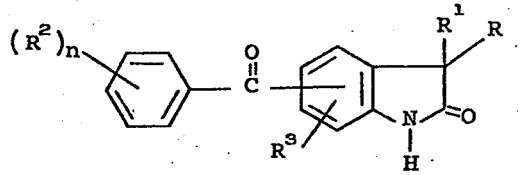

wherein:
R is selected from the group consisting of hydrogen, lower-alkyl or methylthio,
$R^1$ is selected from the group consisting of hydrogen or lower-alkyl,
$R^2$ is selected from the group consisting of lower-alkyl, lower-alkoxy, halogen, nitro or trifluoromethyl,
$R^3$ is selected from the group consisting of hydrogen, halogen or lower alkoxy, $n$ is 0, 1 or 2, and
(b) a pharmaceutically acceptable carrier therefor.

25. A composition according to claim 24 wherein the active ingredient is 5-benzoylindolin-2-one.

26. A composition according to claim 24 wherein the active ingredient is 7-benzoylindolin-2-one.

27. A composition according to claim 24 wherein the active ingredient is 3-methyl-5-benzoylindolin-2-one.

28. A composition according to claim 24 wherein the active ingredient is 3-(n-butyl)-5-benzoylindolin-2-one.

29. A composition according to claim 24 wherein the active ingredient is 7-benzoyl-5-chloroindolin-2-one.

30. A composition according to claim 24 wherein the active ingredient is 7-benzoyl-5-methoxyindolin-2-one.

31. A composition according to claim 24 wherein the active ingredient is 7-(4-chlorobenzoyl)indolin-2-one.

* * * * *